(12) United States Patent
Chun et al.

(10) Patent No.: US 9,629,694 B2
(45) Date of Patent: Apr. 25, 2017

(54) PRECISION CONFIGURATION OF A COMPONENT

(71) Applicant: Hankookin, Inc., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC., Raleigh, NC (US)

( * ) Notice: Subject to any disclaimer, the term of this patent is extended or adjusted under 35 U.S.C. 154(b) by 334 days.

(21) Appl. No.: 14/298,961

(22) Filed: Jun. 8, 2014

(65) Prior Publication Data
US 2014/0360999 A1    Dec. 11, 2014

Related U.S. Application Data

(60) Provisional application No. 61/832,969, filed on Jun. 10, 2013.

(51) Int. Cl.
| | |
|---|---|
| *A61C 7/04* | (2006.01) |
| *B21F 1/00* | (2006.01) |
| *A61C 7/00* | (2006.01) |
| *B21F 99/00* | (2009.01) |
| *A61C 7/28* | (2006.01) |

(52) U.S. Cl.
CPC ............... *A61C 7/04* (2013.01); *A61C 7/002* (2013.01); *B21F 1/002* (2013.01); *B21F 1/008* (2013.01); *B21F 99/00* (2013.01); *A61C 7/28* (2013.01)

(58) Field of Classification Search
CPC . A61C 7/04; A61C 7/002; B21F 1/002; B21F 1/008; B21F 99/00
USPC ....... 219/227, 229, 230, 236, 237, 238, 240, 219/241
See application file for complete search history.

(56) References Cited

U.S. PATENT DOCUMENTS

| | | | |
|---|---|---|---|
| 5,050,089 A * | 9/1991 | Stelson | B21D 7/14 700/165 |
| 2011/0104629 A1* | 5/2011 | Navarro | A61C 7/04 433/4 |

\* cited by examiner

*Primary Examiner* — David Angwin
*Assistant Examiner* — Justin Dodson
(74) *Attorney, Agent, or Firm* — Ash Tankha; Lipton, Weinberger & Husick

(57) ABSTRACT

A precision configuration system includes a plier device having clasp members, a heat transfer clamp member, a bending force transducer, and a temperature controller. One clasp member has a single jaw tooth that contacts and heats a component, for example, a wire positioned by a component holder and accommodated within a receptacle defined between double jaw teeth of the other clasp member. The heat transfer clamp member includes a heating coil that generates and transfers heat to the single jaw tooth. The bending force transducer controls magnitude and direction of bending forces applied by the plier device to precision bend and reshape the component at one or more bending points on the component based on force commands received from a component configuration computer system. The temperature controller controls the generation and transfer of heat to the single jaw tooth to facilitate temperature controlled, precision bending and reshaping of the component.

5 Claims, 11 Drawing Sheets

PRECISION CONFIGURATION OF A COMPONENT

CROSS REFERENCE TO RELATED APPLICATIONS

This application claims priority to and the benefit of provisional patent application No. 61/832,969 titled "Temperature Controlled Plier", filed in the United States Patent and Trademark Office on Jun. 10, 2013. The specification of the above referenced patent application is incorporated herein by reference in its entirety.

BACKGROUND

Components, for example, esthetic prosthetic clasps and orthodontic wires that are used in dental offices to reconfigure teeth and direct the movement of teeth against which these components are applied, generally longitudinal wires used in other applications, etc., hereinafter "components", are made from diverse materials, for example, metal, metal alloy, plastic, fiber glass, etc. These components often need to be precision bent and configured to a desired configuration. For example, in a removable orthodontic appliance, one or more arch wires are infused and rigidly anchored within a lingual side of an arch tray. These arch wires need to be precision bent and reshaped at precise angles to produce a desired force on the teeth to be moved. Three prong wire pliers or devices containing three prong wire pliers are instruments typically used by dentists to reshape metal clasps and metal wires. However, bending metal or plastic wires and clasps into exact three-dimensional shapes required by dentists using the three prong wire pliers or devices containing the three prong wire pliers can be difficult due to precision requirements and the physical properties of the wire and clasp material. For example, at room temperature, plastic and nickel titanium wires typically return to their original shapes. The shape of a plastic wire or a nickel titanium wire can be changed only when the temperature of the wire is increased to a range that allows a non-elastic movement of atoms and molecules of the wire. Therefore, there is a need to provide an instrument and a system that precisely bends components, for example, wires, clasps, etc., and controls the temperature of the components to facilitate precision bending and reshaping of the components.

Hence, there is a long felt but unresolved need for a method and a precision configuration system comprising a precision bending and reshaping apparatus that bends and reshapes a component without melting or damaging the component by precision control of the fabrication of the component at preset controlled temperatures.

SUMMARY OF THE INVENTION

This summary is provided to introduce a selection of concepts in a simplified form that are further disclosed in the detailed description of the invention. This summary is not intended to identify key or essential inventive concepts of the claimed subject matter, nor is it intended for determining the scope of the claimed subject matter.

Disclosed herein is a method and a precision configuration system comprising a precision bending and reshaping apparatus for temperature controlled, precision bending and reshaping of a component, for example, an orthodontic wire, a prosthetic clasp, etc., to a desired configuration to address the above mentioned needs. The precision bending and reshaping apparatus disclosed herein comprises a plier device, a heat transfer clamp member, and a temperature controller. The plier device comprises a first clasp member and a second clasp member. The first clasp member comprises double jaw teeth connected to a first jaw arm. The double jaw teeth of the first clasp member define a receptacle for positioning and accommodating the component. The second clasp member is hingedly connected to the first clasp member. The second clasp member comprises a single jaw tooth connected to a second jaw arm. The single jaw tooth is configured to contact and electro-thermally heat the component positioned and accommodated within the receptacle defined between the double jaw teeth of the first clasp member.

The heat transfer clamp member is detachably connected to the second clasp member of the plier device. The heat transfer clamp member comprises a clamping element, an elongate member, and a heating coil. The clamping element is configured to engageably connect with the single jaw tooth of the second clasp member. The elongate member extends from a lower end of the clamping element. The elongate member houses the heating coil. The heating coil generates heat and transfers the generated heat to the single jaw tooth of the second clasp member via the clamping element to heat the component positioned and accommodated within the receptacle defined between the double jaw teeth of the first clasp member. The temperature controller is electrically connected to the heating coil of the heat transfer clamp member. The temperature controller controls the generation of heat by the heating coil, thereby controlling the transfer of the generated heat to the single jaw tooth of the second clasp member to heat the component to a threshold heating temperature of a material of the component and facilitate the temperature controlled, precision bending and reshaping of the component in contact with the single jaw tooth of the second clasp member to a desired configuration.

The precision configuration system further comprises a container of a predefined shape, a component holder, a bending force transducer, and a component configuration computer system. The container comprises an inner space and an opening positioned on a side of the container. The component holder is positioned in the inner space of the container. The component holder comprises a sleeve axially positioned and removably attached to the opening of the container. The sleeve of the component holder receives, advances, and positions the component in the receptacle of the plier device positioned within the inner space of the container. The bending force transducer is positioned within the inner space of the container and is operably connected to the first clasp member and the second clasp member of the plier device. The bending force transducer controls the magnitude and direction of bending forces applied by the first clasp member and the second clasp member to precision bend and reshape the component at one or more bending points on the component based on force commands received from the component configuration computer system.

In one or more various aspects, related systems include but are not limited to circuitry and/or programming for effecting the methods referenced herein; the circuitry and/or programming can be virtually any combination of hardware, software, and/or firmware configured to effect the herein-referenced methods depending upon the design choices of a system designer. Also, various structural elements may be employed depending on the design choices of the system designer.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing carries over to the description of that method step or structure shown by that same numeral in any subsequent drawing herein.

DETAILED DESCRIPTION OF THE INVENTION

Figure 1A:
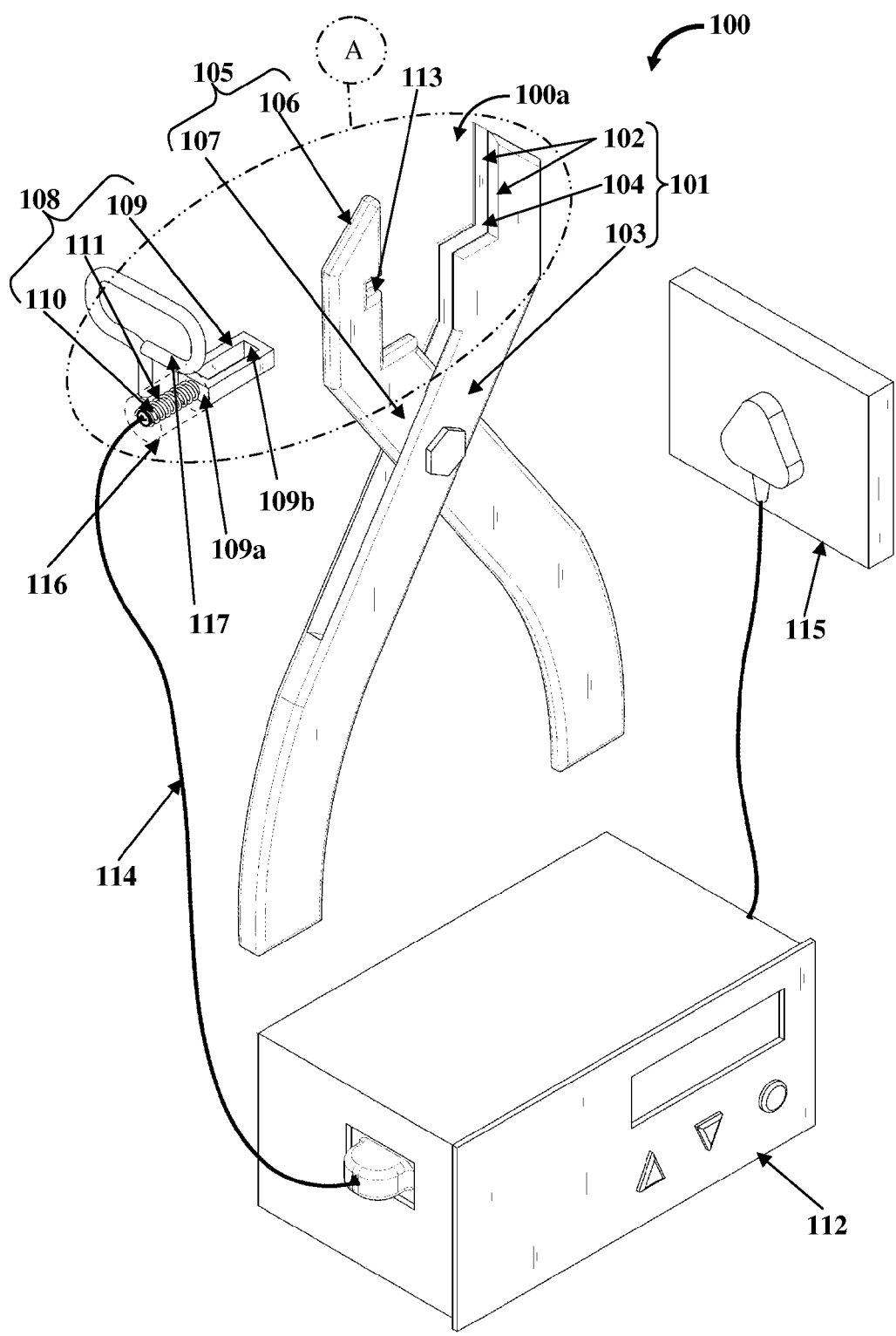
FIG. 1A exemplarily illustrates a perspective view of a precision bending and reshaping apparatus for temperature controlled, precision bending and reshaping of a component.
Figure 1B:
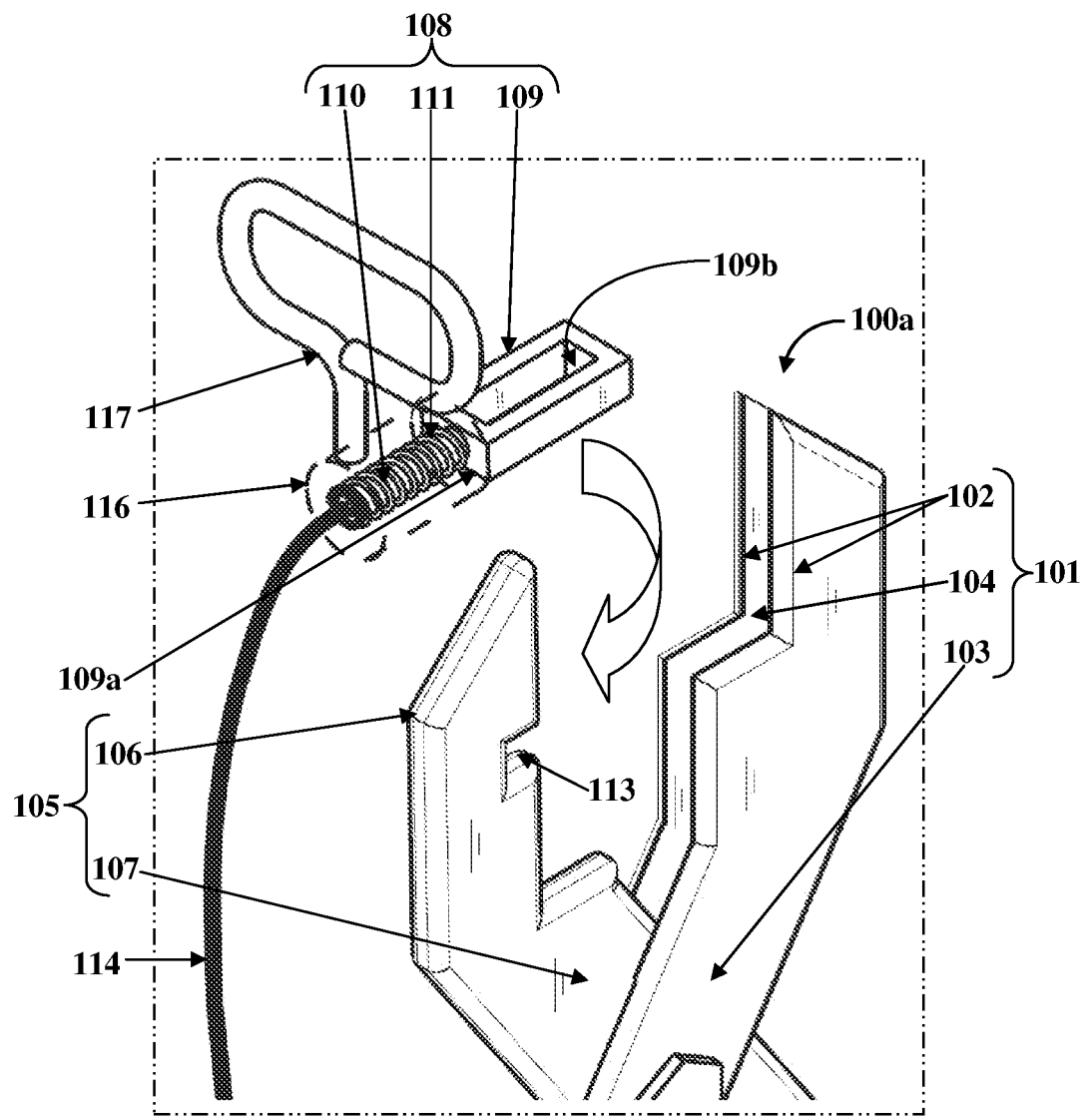
FIG. 1B exemplarily illustrates an enlarged view of a portion marked A in FIG. 1A.
Figure 3A:
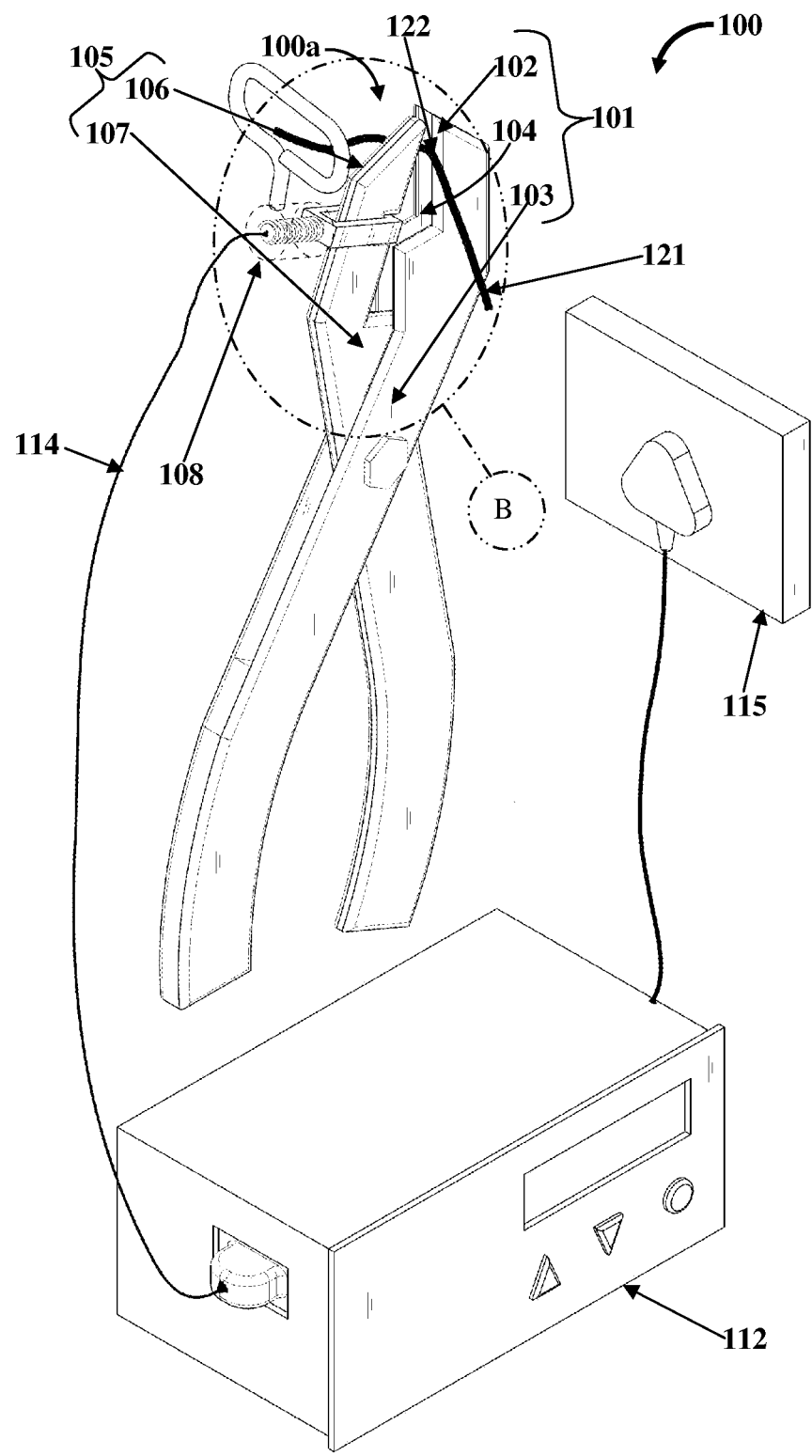
FIG. 3A exemplarily illustrates a perspective view of the precision bending and reshaping apparatus, showing a component positioned and accommodated in a receptacle defined between double jaw teeth of a first clasp member of the plier device for temperature controlled, precision bending and reshaping of the component.
Figure 3B:
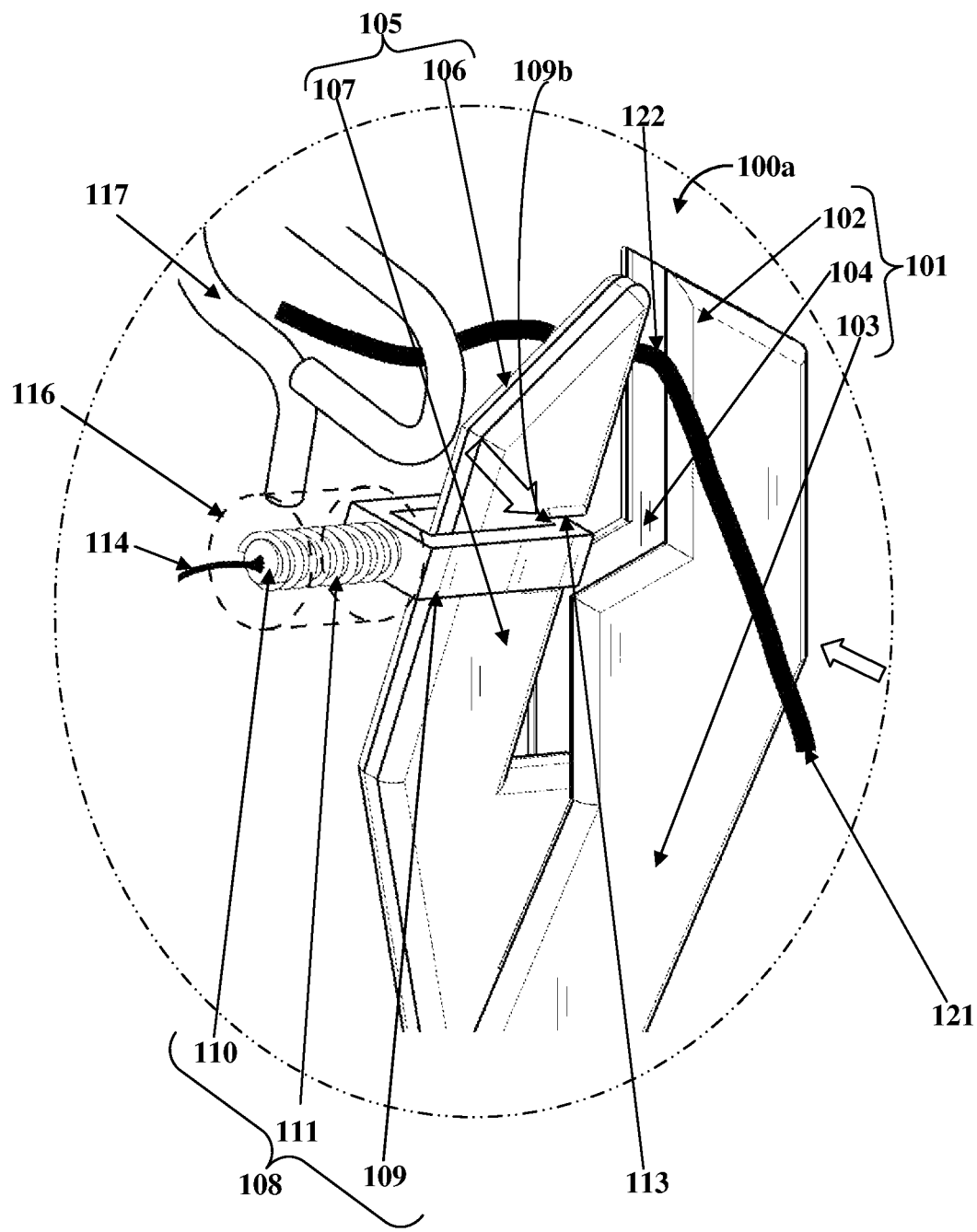
FIG. 3B exemplarily illustrates an enlarged view of a portion marked B in FIG. 3A.

FIG. 1A exemplarily illustrates a perspective view of a precision bending and reshaping apparatus 100 for temperature controlled, precision bending and reshaping of a component 121 exemplarily illustrated in FIGS. 3A-3B, and FIG. 1B exemplarily illustrates an enlarged view of a portion marked A in FIG. 1A. As used herein, the term "component" refers to an object, for example, a plastic clasp, a metal wire such as an orthodontic wire, etc., that is malleable and/or ductile and can be positioned between a first clasp member 101 and a second clasp member 105 of a plier device 100a to be precision bent and reshaped to a desired configuration. For example, the precision bending and reshaping apparatus 100 disclosed herein is used for bending a plastic component, for example, a plastic clasp section of a prosthetic clasp to enable the prosthetic clasp to achieve a better contact force with an attached structure within an oral cavity of a patient.

The precision bending and reshaping apparatus 100 disclosed herein comprises a plier device 100a, a heat transfer clamp member 108, and a temperature controller 112. The plier device 100a is implemented as a three jaw apparatus connected to the temperature controller 112 via the heat transfer clamp member 108 to facilitate control of heat to the component 121 exemplary illustrated in FIGS. 3A-3B. The plier device 100a comprises a first clasp member 101 and a second clasp member 105. The first clasp member 101 comprises double jaw teeth 102 connected to a first jaw arm 103. The double jaw teeth 102 of the first clasp member 101 define a receptacle 104 for positioning and accommodating the component 121. The second clasp member 105 is hingedly connected to the first clasp member 101. The second clasp member 105 comprises a single jaw tooth 106 connected to a second jaw arm 107. The single jaw tooth 106 of the second clasp member 105 is configured to contact and electro-thermally heat the component 121 positioned and accommodated within the receptacle 104 defined between the double jaw teeth 102 of the first clasp member 101. For dental applications, the plier device 100a is sterilizable by standard dental sterilization methods. The plier device 100a weighs, for example, about 400 grams. The dimensions of the plier device 100a are, for example, about 15 centimeters (cm) long and about 8 cm wide, and with a thickness of about 1 cm.

The heat transfer clamp member 108 of the precision bending and reshaping apparatus 100 disclosed herein is detachably connected to the second clasp member 105 of the plier device 100a as exemplarily illustrated in FIGS. 3A-3B. The heat transfer clamp member 108 comprises a clamping element 109, an elongate member 110, and a heating coil 111. The clamping element 109 is configured to engageably connect with the single jaw tooth 106 of the second clasp member 105 as exemplarily illustrated in FIGS. 3A-3B. The elongate member 110 of the heat transfer clamp member 108 extends from a lower end 109a of the clamping element 109 and houses the heating coil 111. The heating coil 111 housed on the elongate member 110 generates heat by controlled electric power supplied from an electric power supply 115 to the heating coil 111 via the temperature controller 112 and transfers the generated heat to the single jaw tooth 106 of the second clasp member 105 via the clamping element 109 to heat the component 121 positioned and accommodated within the receptacle 104 defined between the double jaw teeth 102 of the first clasp member 101 and allow the component 121 to be precision bent and reshaped under temperature controlled conditions.

As exemplarily illustrated in FIG. 1B, in an embodiment, the single jaw tooth 106 of the second clasp member 105 of the plier device 100a comprises a slot 113 of a predefined shape, for example, a generally rectangular shape for connecting the clamping element 109 of the heat transfer clamp member 108. In an embodiment, the heat transfer clamp member 108 is engaged on the single jaw tooth 106 of the second clasp member 105 by mounting the clamping element 109 of the heat transfer clamp member 108 on the single jaw tooth 106 and accommodating an inner section 109b of the clamping element 109 in the slot 113 positioned on the single jaw tooth 106 for maintaining a fixed operable contact of the clamping element 109 with the single jaw tooth 106 while electro-thermally heating the single jaw tooth 106 as indicated by the arrow in FIG. 1B and as exemplarily illustrated in FIGS. 3A-3B.

The temperature controller 112 of the precision bending and reshaping apparatus 100 is electrically connected to the heating coil 111 of the heat transfer clamp member 108 via a power cord 114 and is connected to the electric power supply 115 as exemplarily illustrated in FIG. 1A. The temperature controller 112 controls the generation of heat by the heating coil 111, thereby controlling the heat transferred to the single jaw tooth 106 of the second clasp member 105 of the plier device 100*a* to heat the component 121 to a threshold heating temperature of a material of the component 121 and facilitate the temperature controlled, precision bending and reshaping of the component 121 in contact with the single jaw tooth 106 of the second clasp member 105 to a desired configuration. The temperature controller 112 thereby controls the temperature of the single jaw tooth 106. An insulating cover 116 is provided around the heating coil 111 housed on the elongate member 110 of the heat transfer clamp member 108 to preclude a user's hand from coming in direct contact with the heated heating coil 111. A handle 117 is fixedly positioned over the insulating cover 116 for a user to hold and engage the heat transfer clamp member 108 on the single jaw tooth 106 of the second clasp member 105. The insulating cover 116 and the handle 117 are made of insulating materials, for example, plastic, rubber, etc. In an embodiment, the temperature controller 112 can be preset to heat the component 121 to its threshold heating temperature to facilitate the precision bending and reshaping of the component 121.

Figure 2:
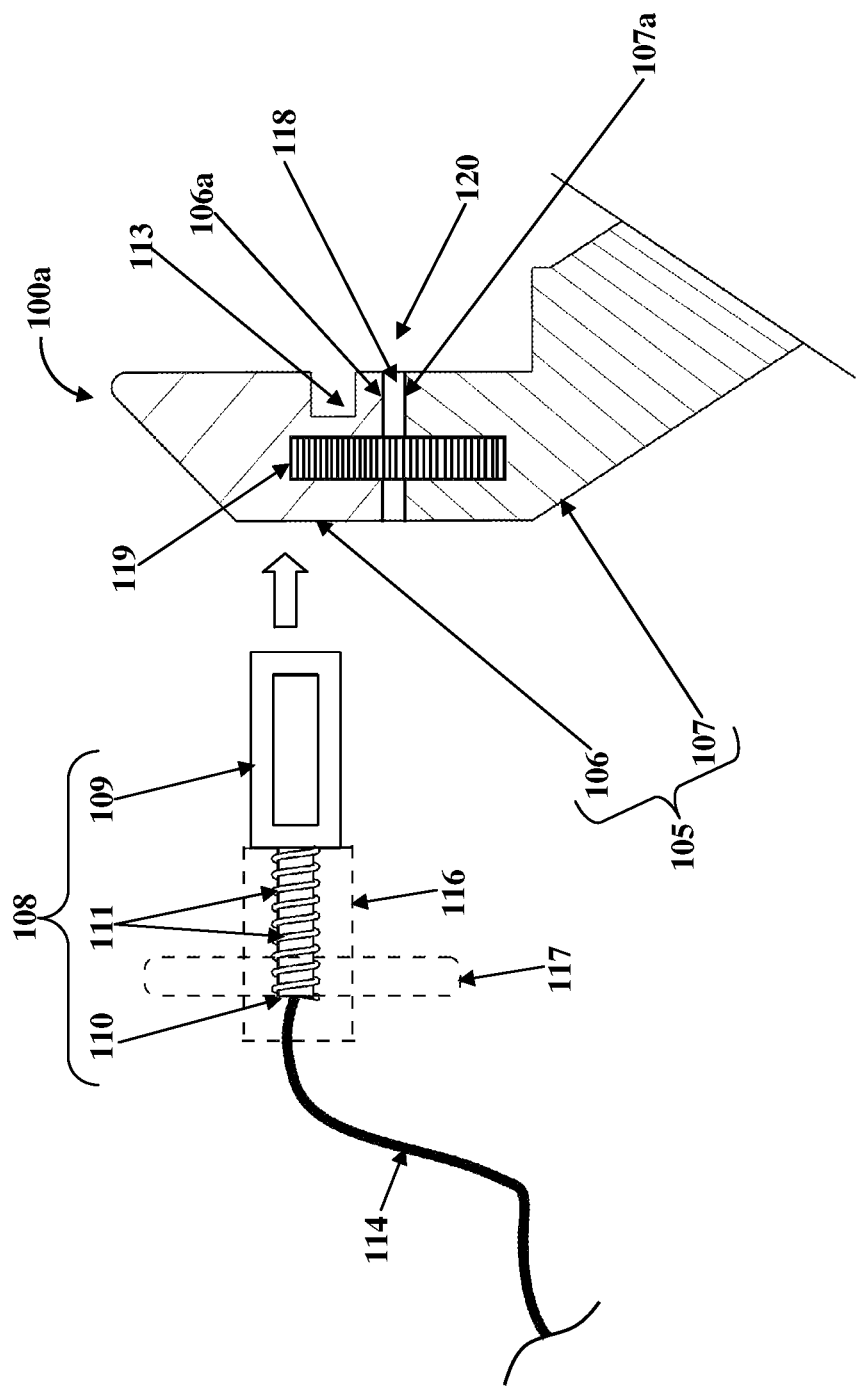
FIG. 2 exemplarily illustrates a partial sectional view of a second clasp member of a plier device and a top perspective view of a heat transfer clamp member detachably connectable to the second clasp member.

FIG. 2 exemplarily illustrates a partial sectional view of a second clasp member 105 of the plier device 100*a* exemplarily illustrated in FIG. 1A, and a top perspective view of the heat transfer clamp member 108 detachably connectable to the second clasp member 105. The plier device 100*a* further comprises a heat insulation member 118 connected between the single jaw tooth 106 and the second jaw arm 107 of the second clasp member 105 using a screw connector 119. The heat insulation member 118 insulates the second jaw arm 107 from the heat transferred to the single jaw tooth 106 by the heat transfer clamp member 108. In an embodiment, the screw connector 119 is positioned at a mid-section 120 between the single jaw tooth 106 and the second jaw arm 107 of the second clasp member 105. The heat insulation member 118 of the second clasp member 105 is operably positioned between a lower end 106*a* of the single jaw tooth 106 and an upper end 107*a* of the second jaw arm 107 of the second clasp member 105. In an embodiment, the clamping element 109 of the heat transfer clamp member 108 is customizable to fittingly clamp around the single jaw tooth 106 of the second clasp member 105 to achieve maximum surface contact with the single jaw tooth 106, thereby facilitating a maximum transfer of the heat generated by the heating coil 111 to the single jaw tooth 106.

FIG. 3A exemplarily illustrates a perspective view of the precision bending and reshaping apparatus 100, and FIG. 3B exemplarily illustrates an enlarged view of a portion marked B in FIG. 3A. FIG. 3A shows a component 121, for example, a metal wire positioned and accommodated in the receptacle 104 defined between the double jaw teeth 102 of the first clasp member 101 of the plier device 100*a* for temperature controlled, precision bending and reshaping of the component 121. The double jaw teeth 102 accommodates and positions the component 121 in the receptacle 104 and the single jaw tooth 106 that opposedly faces the double jaw teeth 102 bends the component 121 at a bending point 122 on the component 121. On application of pressure on the first jaw arm 103 of the first clasp member 101 and the second jaw arm 107 of the second clasp member 105, the single jaw tooth 106 contacts and precision bends the component 121 at the bending point 122 to the desired configuration.

As exemplarily illustrated in FIG. 3B, the clamping element 109 of the heat transfer clamp member 108 is mounted on the single jaw tooth 106 of the second clasp member 105 by attaching the inner section 109*b* of the clamping element 109 in the slot 113 positioned on the single jaw tooth 106 to engage the heat transfer clamp member 108 on the single jaw tooth 106. The single jaw tooth 106 of the second clasp member 105 is heated separately and independent of the first clasp member 101. The heated single jaw tooth 106 of the second clasp member 105 contacts the component 121 positioned and accommodated in the receptacle 104 defined between the double jaw teeth 102 of the first clasp member 101 at the bending point 122 of the component 121. The temperature of the component 121 at the bending point 122 is increased by transferring the heat generated by the heating coil 111 of the heat transfer clamp member 108 to the bending point 122 of the component 121 via the heated single jaw tooth 106, thereby facilitating the component 121 to be more precisely bent and reshaped at the bending point 122. When the temperature of the component 121 reaches the temperature at which the component 121 can be bent and reshaped, the component 121 is precisely bent and permanently reshaped to the desired configuration by the user using the precision bending and reshaping apparatus 100.

The component 121 is bent or reshaped by heating the component 121 to a temperature, herein referred to as a "threshold heating temperature", at which the material of the component 121 becomes malleable. Once the threshold heating temperature of the component 121 is reached, the component 121 is bent or reshaped to the desired configuration and thereafter cooled to obtain the configuration desired by the user. When the heating coil 111 attains the threshold heating temperature of the component 121, the temperature controller 112 terminates the generation of heat at the heating coil 111 to avoid overheating and damage of the component 121. When the temperature of the component 121 falls below the threshold heating temperature, the temperature controller 112 resumes the generation of heat by the heating coil 111 to allow the component 121 to be precisely bent and reshaped. The component 121 is thereafter cooled to obtain the desired configuration of the component 121.

Consider an example of an esthetic orthodontic clasp (not shown) comprising a metal clasp section and a plastic clasp section. The thickness of an orthodontic clasp is, for example, from about 0.5 mm to about 3 mm. The precision bending and reshaping apparatus 100 exemplarily illustrated and disclosed in the detailed description of FIGS. 1A-1B, is used to bend the plastic clasp section of the orthodontic clasp by controlling the temperature of the plastic clasp section to allow the plastic clasp section to be precisely bent and reshaped by a user to the configuration desired by the user without overheating or damaging the plastic clasp section. The plastic clasp section of the orthodontic clasp is positioned within the receptacle 104 defined between the double jaw teeth 102 of the first clasp member 101 of the plier device 100*a* exemplarily illustrated in FIGS. 1A-1B and FIG. 3B. The single jaw tooth 106 of the second clasp member 105 contacts and heats the plastic clasp section positioned in the receptacle 104. The heat transfer to the plastic clasp section allows the user to precisely bend and reshape the plastic clasp section once the temperature of the plastic clasp section reaches the threshold heating temperature range; or, in an embodiment, a temperature range set by the user. When the plastic clasp section attains the desired configuration, the heat generation by the heating coil 111 of the heat transfer clamp member 108 is terminated by the temperature controller 112. The heated portion of the plastic clasp section is thereafter allowed to cool to obtain the permanent, desired configuration of the plastic clasp section.

Figure 4A:
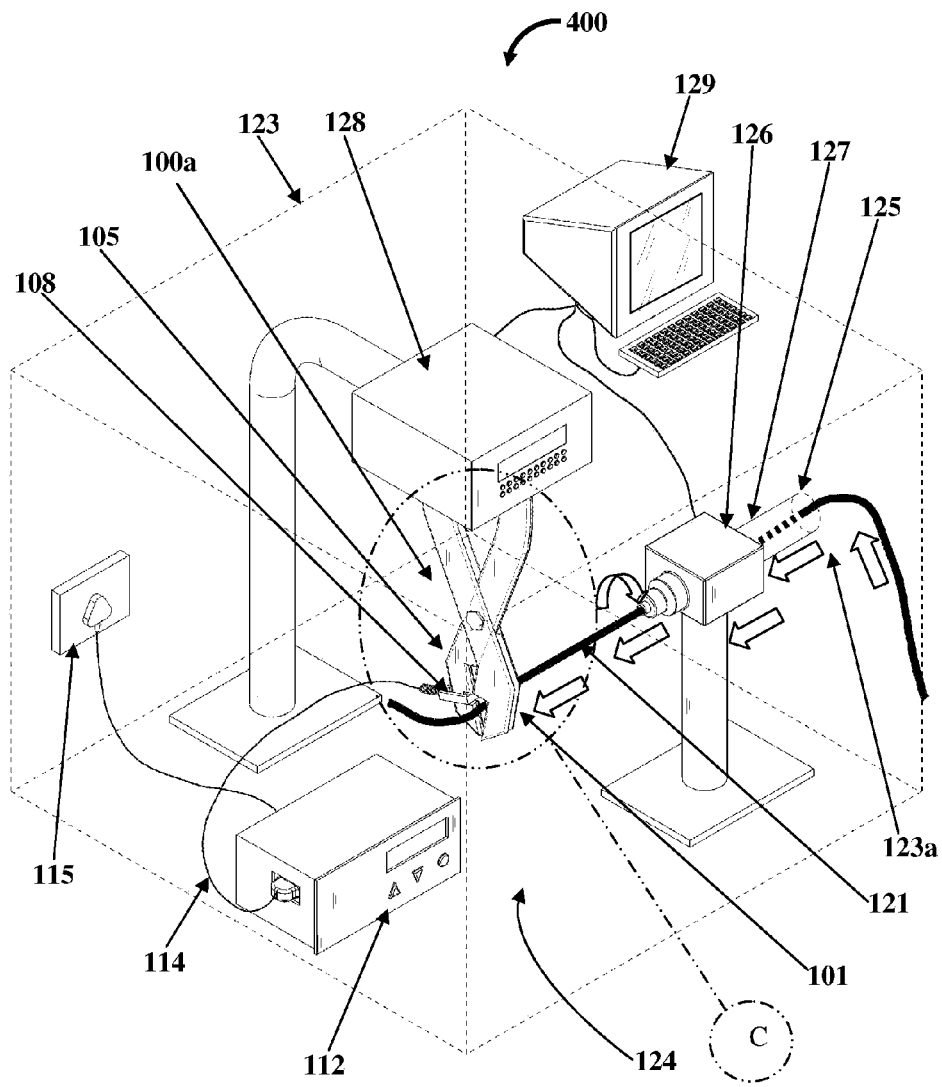
FIG. 4A exemplarily illustrates an isometric view of a precision configuration system.
Figure 4B:
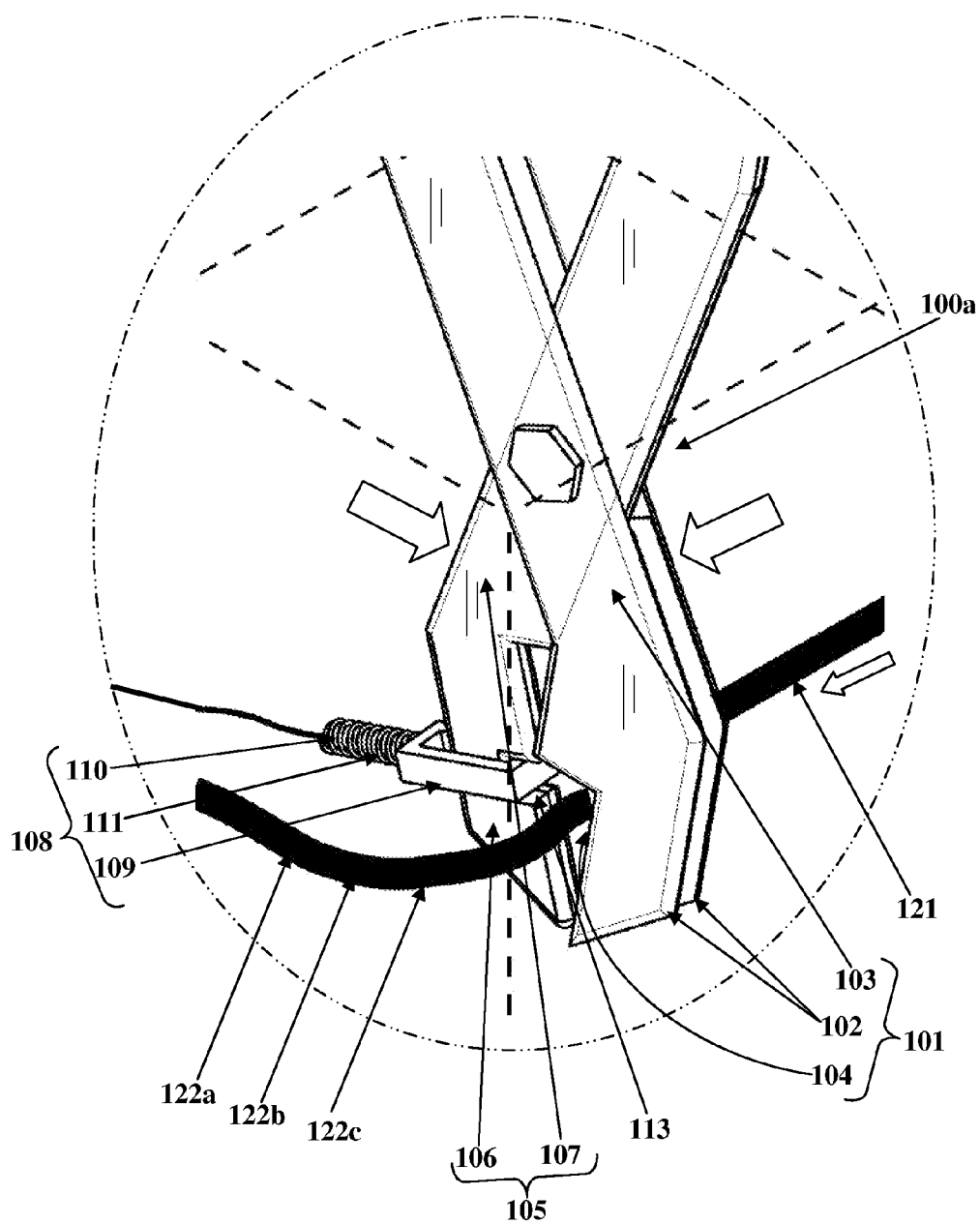
FIG. 4B exemplarily illustrates an enlarged view of a portion marked C in FIG. 4A, showing a clamping element of the heat transfer clamp member mounted on a single jaw tooth of the second clasp member of the plier device and a component positioned in the receptacle defined between the double jaw teeth of the first clasp member of the plier device for temperature controlled, precision bending and reshaping of the component.

FIG. 4A exemplarily illustrates an isometric view of a precision configuration system 400, and FIG. 4B exemplarily illustrates an enlarged view of a portion marked C in FIG. 4A. FIG. 4B shows the clamping element 109 of the heat transfer clamp member 108 mounted on the single jaw tooth 106 of the second clasp member 105 of the plier device 100a and a component 121 positioned in the receptacle 104 defined between the double jaw teeth 102 of the first clasp member 101 of the plier device 100a for temperature controlled, precision bending and reshaping of the component 121. In an embodiment, the component 121 to be bent and reshaped is an orthodontic wire 501 exemplarily illustrated in FIG. 5. The precision configuration system 400 disclosed herein comprises a container 123 of a predefined shape, for example, a cubical shape, a cuboidal shape, etc., a component holder 126, the plier device 100a, the heat transfer clamp member 108, a bending force transducer 128, the temperature controller 112, and a component configuration computer system 129. The plier device 100a, the heat transfer clamp member 108, and the temperature controller 112 constitute the precision bending and reshaping apparatus 100 exemplarily illustrated in FIG. 1A. The container 123 comprises an inner space 124 and an opening 125 positioned on a side 123a of the container 123. The component holder 126 is positioned in the inner space 124 of the container 123. The component holder 126 comprises a sleeve 127 axially positioned and removably attached to the opening 125 of the container 123. The sleeve 127 of the component holder 126 receives, advances, and positions the component 121 in the receptacle 104 of the plier device 100a positioned within the inner space 124 of the container 123 as exemplarily illustrated in FIG. 4B. The component holder 126 holds the component 121 and advances the component 121 such that the bending points 122a, 122b, and 122c exemplarily illustrated in FIG. 4B, about which the component 121 is to be precision bent and reshaped, are held at a predefined position between the double jaw teeth 102 and the single jaw tooth 106 of the plier device 100a.

The heat transfer clamp member 108 is detachably connected to the second clasp member 105 of the plier device 100a in the inner space 124 of the container 123. The bending force transducer 128 is positioned within the inner space 124 of the container 123 and is operably connected to the first clasp member 101 and the second clasp member 105 of the plier device 100a. The bending force transducer 128 controls the magnitude and direction of bending forces applied by the first clasp member 101 and the second clasp member 105 to precision bend and reshape the component 121 at one or more of multiple bending points 122a, 122b, 122c, etc., on the component 121 based on force commands received from the component configuration computer system 129. The bending force transducer 128 applies bending forces in directions shown by the arrows in FIG. 4B, on the first clasp member 101 and the second clasp member 105 of the plier device 100a to grip, bend, and reshape the component 121 at the bending points, for example, 122a, 122b, 122c, etc. In an example, the component 121 is first placed between the double jaw teeth 102 and the single jaw tooth 106 of the plier device 100a, such that the bending point 122a is adjacent to and in line with the single jaw tooth 106. The bending force transducer 128 activates the double jaw teeth 102 and the single jaw tooth 106 to exert the precise force needed to produce a desired design curvature at the bending point 122a. Once the bending process is completed, the component holder 126 advances the component 121 to the next bending point 122b as indicated by the arrows in FIG. 4A.

The temperature controller 112 is positioned within the inner space 124 of the container 123 and is electrically connected to the heating coil 111 of the heat transfer clamp member 108 via the power cord 114 exemplarily illustrated in FIG. 4A. The temperature controller 112 is powered by the electric power supply 115 exemplarily illustrated in FIG. 4A. The temperature controller 112 controls the generation of heat by the heating coil 111 of the heat transfer clamp member 108 to control the transfer of the generated heat to the single jaw tooth 106 of the second clasp member 105 to allow the component 121 to attain about the threshold heating temperature of the material of the component 121, which facilitates the component 121 in contact with the single jaw tooth 106 to be precision bent and reshaped to the desired configuration.

The component configuration computer system 129 comprises at least one processor configured to calculate the bending force data comprising, for example, a position, a direction, and a magnitude of each of the bending forces to be applied by the first clasp member 101 and the second clasp member 105 of the plier device 100a to each bending point 122a, or 122b, or 122c exemplarily illustrated in FIG. 4B, on the component 121 using a three-dimensional first derivative D' and a three-dimensional second derivative D" of a curvature of the component 121. In an embodiment, the component configuration computer system 129 receives three-dimensional images of the component 121 to obtain the three-dimensional curvature of the component 121. The component configuration computer system 129 converts the calculated bending force data at the bending points 122a, 122b, and 122c of the component 121 into force commands, and transmits one or more of the force commands to the component holder 126 and to the bending force transducer 128 that are in operable communication with the component configuration computer system 129 as disclosed in the detailed description of FIG. 5. For example, the component configuration computer system 129 forwards the magnitude of the bending forces to the bending force transducer 128 in the form of force commands, which activates the plier device 100a to produce the exact curvature of the component 121.

In an embodiment, the component holder 126, in communication with the component configuration computer system 129, is further configured to move or rotate in relation to the direction of the bending forces as indicated by the arrows in FIG. 4A, based on the force commands. For example, the component configuration computer system 129 forwards the calculated position and direction of the bending forces in the form of force commands to the component holder 126, which rotates the component 121 to the exact coordinates. The bending forces applied on a component 121, for example, an orthodontic wire 501 exemplarily illustrated in FIG. 5, made of stainless steel, or a removable prosthetic clasp made of a prosthetic material, etc., by the plier device 100a using the bending force transducer 128 is, for example, from about below 1 Newton (N) to about 450 Newton.

Figure 5:
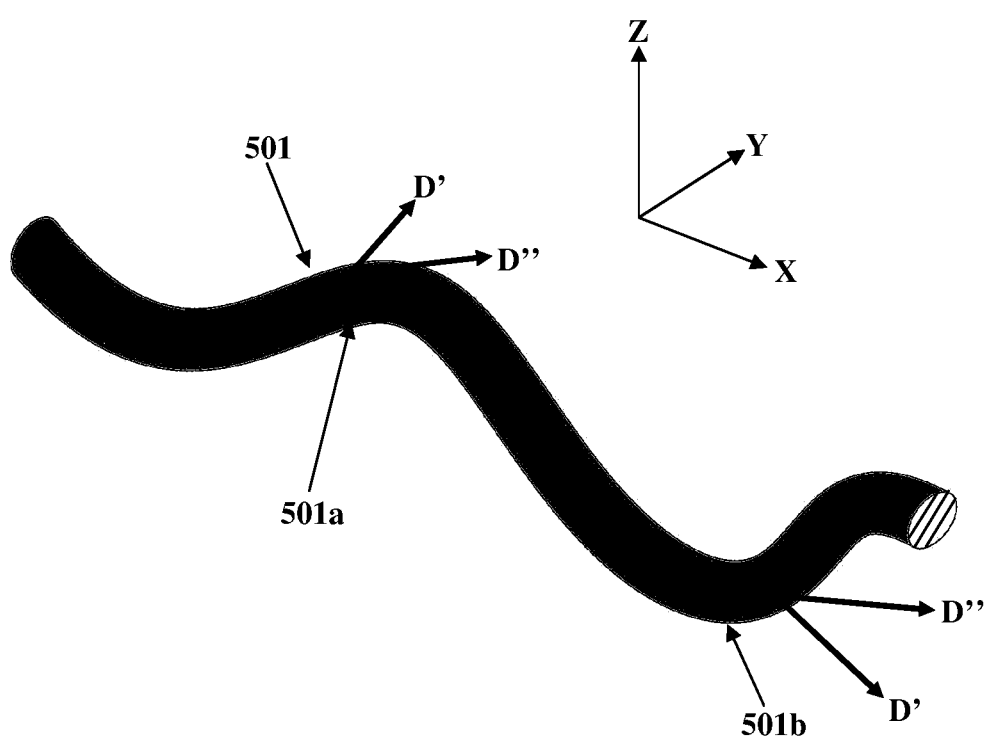
FIG. 5 exemplarily illustrates an enlarged view of a component to be precision bent and reshaped, showing bending points on the component.

FIG. 5 exemplarily illustrates an enlarged view of a component, for example, an orthodontic wire 501, showing bending points 501a and 501b on the orthodontic wire 501. The thickness of the orthodontic wire 501 is, for example, from about 0.1 millimeter (mm) to about 1 mm. In the case of a metal wire such as the orthodontic wire 501, the bending process to produce a precision specific curvature of the orthodontic wire 501 is difficult. With the advance of three-dimensional (3D) imaging technologies, three-dimensional dental images are readily available. The design of the orthodontic wire 501 can be provided in the form of a three-dimensional image of the orthodontic wire 501.

In the first step for the precision bending and reshaping of the orthodontic wire 501, the component configuration computer system 129 exemplarily illustrated in FIG. 4A, determines the curvature of the orthodontic wire 501 at each bending point, for example, 501a or 501b by finding a first derivative D' and a second derivative D" of the wire function W in a three-dimensional space represented by the X-Y-Z axis exemplarily illustrated in FIG. 5. The orthodontic wire 501 is divided into discrete bending points 501a and 501b, a small distance apart from each other, so that the entire orthodontic wire 501 can be reproduced graphically in a three-dimensional space in the component configuration computer system 129 with standard accuracies showing the thickness, length, and degree of curvature along the orthodontic wire 501. The component configuration computer system 129 collects the D' (X, Y, Z), and D" (X, Y, Z) at each of the discrete bending points 501a and 501b of the orthodontic wire 501 to form the wire function W of the orthodontic wire 501. At each of the discrete bending points 501a and 501b:

$$D'(X,Y,Z) = (\partial W/\partial X, \partial W/dY, \partial W/\partial Z), \text{ and}$$

$$D''(X,Y,Z) = (\partial^2 W/\partial X^2, \partial^2 W/\partial Y^2, \partial^2 W/\partial Z^2)$$

The direction of the vector D' (X, Y, Z) determines the direction of the bending force, and D" (X, Y, Z) determines the magnitude or intensity of the bending force to be applied at the discrete bending points 501a and 501b of the orthodontic wire 501. The diameters of the double jaw teeth 102 and the single jaw tooth 106, and the distance between the double jaw teeth 102 and the single jaw tooth 106 or, in an embodiment, the width of the receptacle 104 defined between the double jaw teeth 102 also affect the curvature of the orthodontic wire 501. A software application (not shown) installed in the component configuration computer system 129 and executable by a processor (not shown) is used to convert the first derivative D' (X, Y, Z) and the second derivative D"(X, Y, Z) at each of the discrete bending points 501a and 501b into a series of force commands to interface with the bending force transducer 128 to precision bend the orthodontic wire 501 at each of the discrete bending points 501a and 501b on the orthodontic wire 501.

Figure 6:
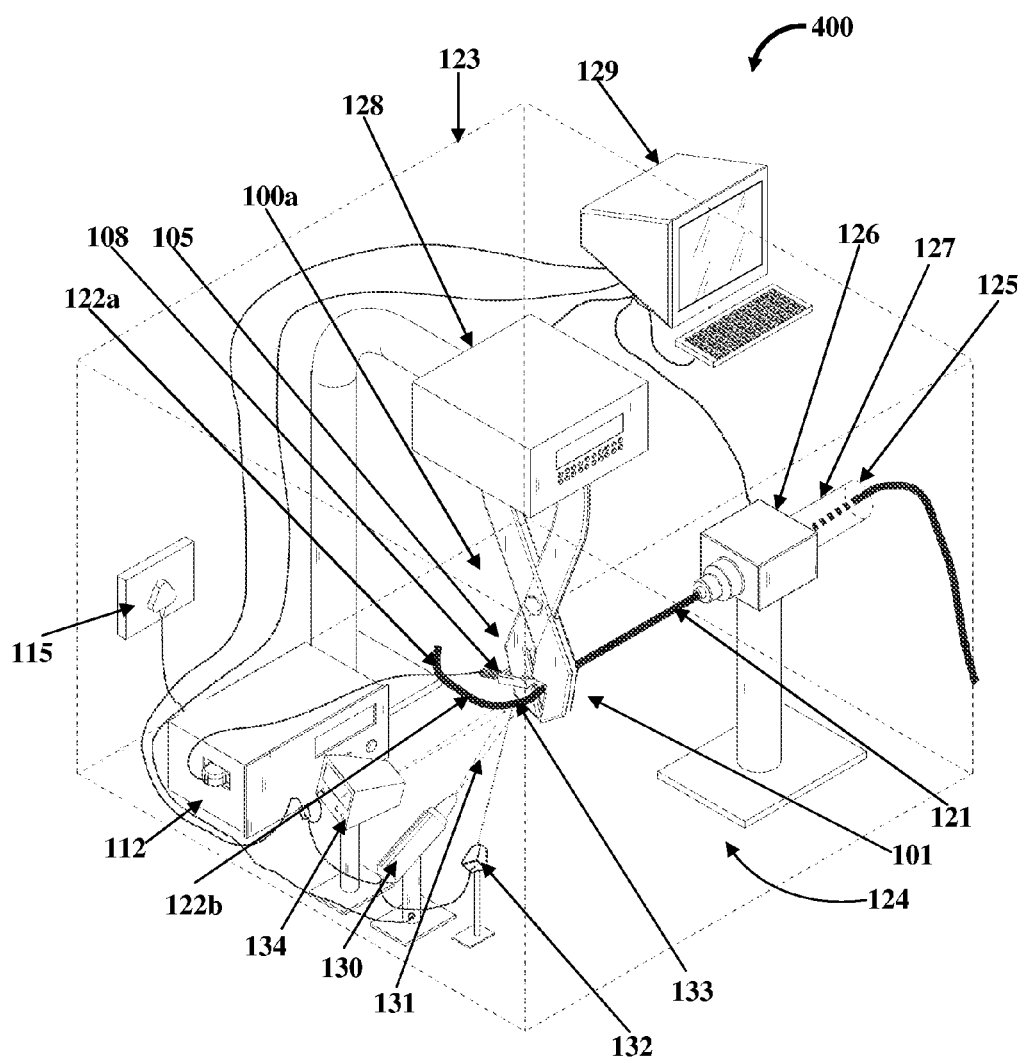
FIG. 6 exemplarily illustrates an isometric view of an embodiment of the precision configuration system.

FIG. 6 exemplarily illustrates an isometric view of an embodiment of the precision configuration system 400. In this embodiment, the precision configuration system 400 disclosed herein further comprises a laser precision heater 130 positioned within the inner space 124 of the container 123. The laser precision heater 130 is operably connected to the component configuration computer system 129. The laser precision heater 130, in communication with the component configuration computer system 129, directs a laser beam 131 to one of the bending points, for example, 122a or 122b on the component 121 and transmits a predefined amount of heat to one of the bending points, for example, 122a or 122b on the component 121 based on one or more of the force commands received from the component configuration computer system 129. In an embodiment, the laser precision heater 130, in communication with the component configuration computer system 129, directs a laser beam 131 to one of the bending points, for example, 122a or 122b on the component 121 and transmits a predefined amount of heat of about the threshold heating temperature of the material of the component 121 to be bent and reshaped, to one of the bending points, for example, 122a or 122b of the component 121 based on one or more of the force commands received from the component configuration computer system 129.

The laser precision heater 130 receives initiation and termination commands from the component configuration computer system 129 to initiate and terminate the transmission of a predefined amount of heat to one of the bending points, for example, 122a or 122b on the component 121 based on one or more of the force commands received from the component configuration computer system 129. In an embodiment, the laser precision heater 130 receives initiation and termination commands from the component configuration computer system 129 to initiate and terminate the transmission of a predefined amount of heat sufficient to increase the temperature of the material of the component 121 to about the threshold heating temperature at one of the bending points, for example, 122a and 122b on the component 121 based on one or more of the force commands received from the component configuration computer system 129. An orthodontic wire 501 exemplarily illustrated in FIG. 5, made, for example, from nickel titanium can only be bent at a temperature much higher than room temperature. If the temperature controller 112 cannot increase the temperature at the bending point 122a or 122b to its threshold heating temperature or another appropriate temperature, the laser precision heater 130 is used to direct the laser beam 131 to the bending point 122a or 122b to deliver an appropriate amount of heat to the component 121 at the bending points 122a and 122b. In an embodiment, the laser precision heater 130 is positioned manually or mechanically to focus the laser beam 131 at the bending points 122a and 122b of the component 121.

In an embodiment, the precision configuration system 400 disclosed herein further comprises a visible laser marker 132, for example, a red cross laser marker, in operable communication with the laser precision heater 130 in the inner space 124 of the container 123. The visible laser marker 132 marks a focal point 133 on the component 121 to focus the laser beam 131 from the laser precision heater 130 to one of the bending points 122a and 122b on the component 121. In an embodiment, the precision configuration system 400 disclosed herein further comprises an infrared temperature detector 134 positioned within the inner space 124 of the container 123. The infrared temperature detector 134 is operably connected to the component configuration computer system 129. The infrared temperature detector 134 is focused at the bending points 122a and 122b on the component 121 to monitor the temperature at the bending points 122a and 122b on the component 121. The infrared temperature detector 134 communicates with the component configuration computer system 129 to adjust the transmission of the predefined amount of heat from the laser beam 131 directed by the laser precision heater 130 to the bending points 122a and 122b on the component 121. If the temperature at the bending points 122a and 122b on the component 121 is below the desired threshold heating temperature, the infrared temperature detector 134 instructs the laser precision heater 130 in communication with the component configuration computer system 129 to continue the transmission of heat to the bending points 122a and 122b of the component 121. If the temperature at the bending points 122a and 122b exceeds the desired threshold heating temperature, the infrared temperature detector 134 instructs the laser precision heater 130 in communication with the component configuration computer system 129 to terminate the transmission of heat to the bending points 122a and 122b of the component 121.

Figure 7A:
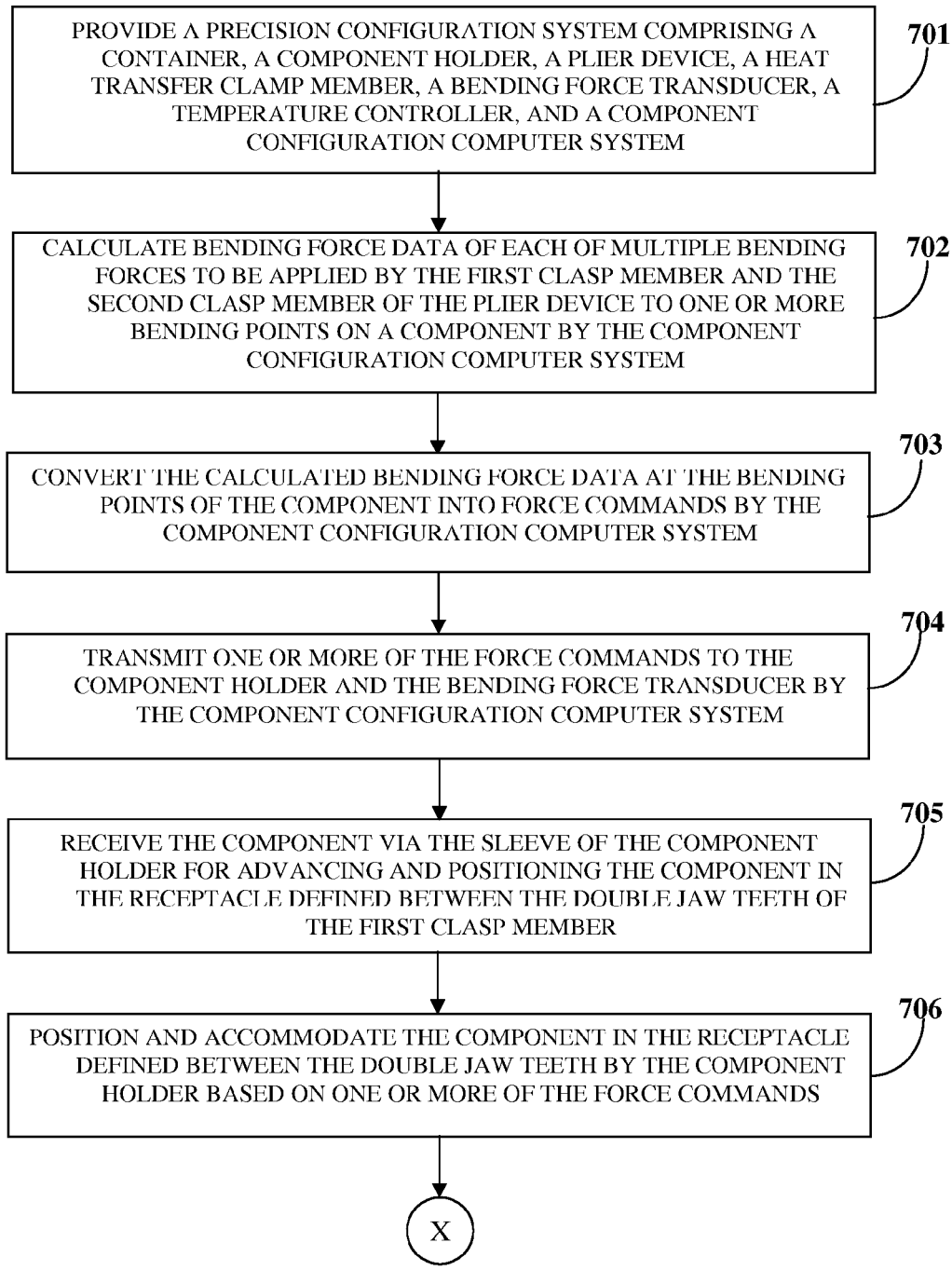
FIGS. 7A-7B illustrate a method for a temperature controlled, precision bending and reshaping of a component.
Figure 7B:
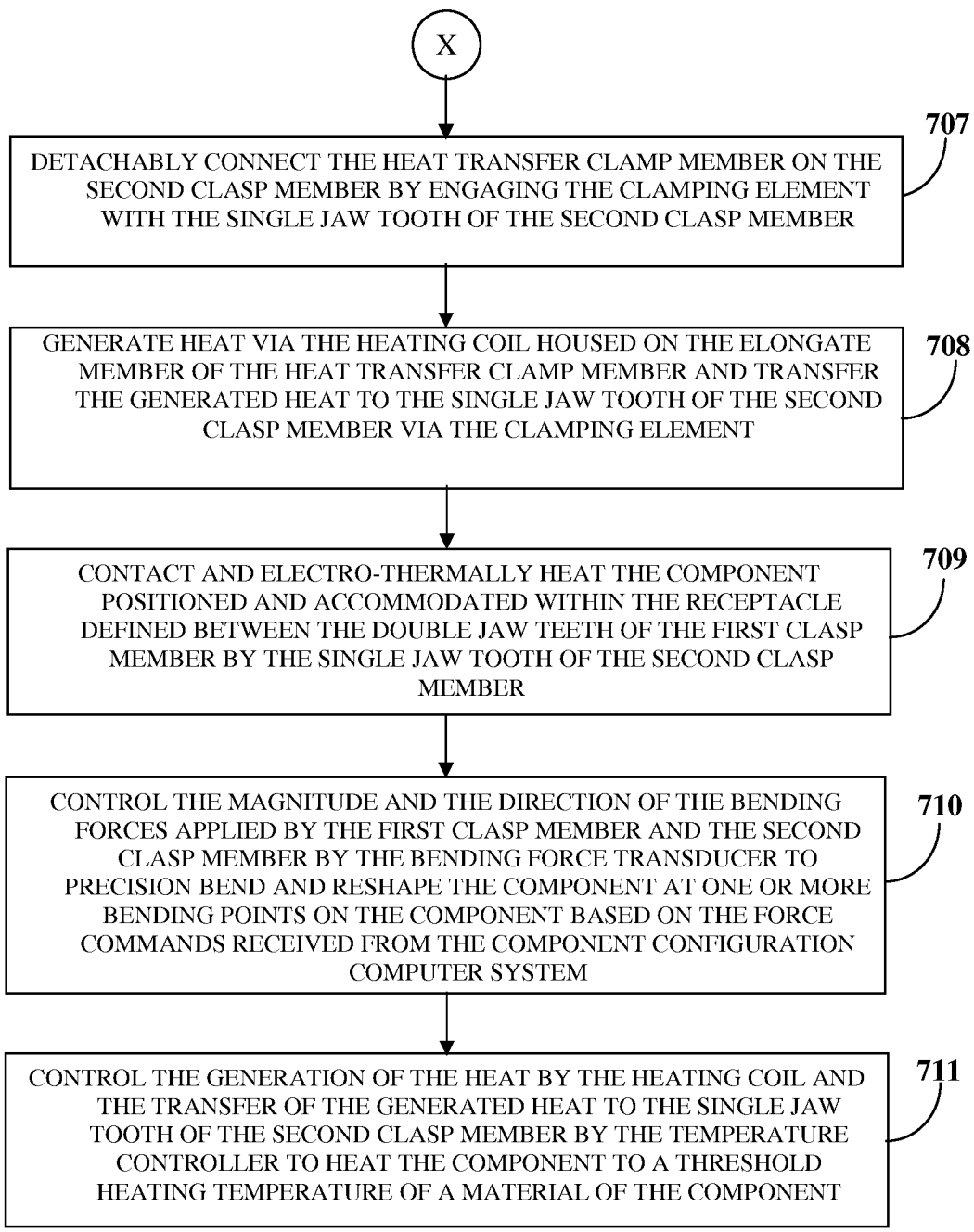

FIGS. 7A-7B illustrate a method for a temperature controlled, precision bending and reshaping of a component 121. The precision configuration system 400 comprising the container 123, the component holder 126, the plier device 100a, the heat transfer clamp member 108, the bending force transducer 128, the temperature controller 112, and the component configuration computer system 129 as exemplarily illustrated in FIGS. 4A-4B and FIG. 6, is provided 701 for a temperature controlled, precision bending and reshaping of a component 121. The component configuration computer system 129 uses a three-dimensional first derivative and a three-dimensional second derivative of a curvature of the component 121 to calculate 702 the bending force data comprising, for example, a position, a direction, and a magnitude of each of multiple bending forces to be applied by the first clasp member 101 and the second clasp member 105 of the plier device 100a, for example, at about the threshold heating temperature of a material of the component 121 to one or more bending points, for example, 122a, 122b, etc., on the component 121. The component configuration computer system 129 converts 703 the calculated bending force data at the bending points 122a and 122b of the component 121 into force commands. The component configuration computer system 129 transmits 704 one or more of the force commands to the component holder 126 and the bending force transducer 128. The sleeve 127 of the component holder 126 receives 705 the component 121 for advancing and positioning the component 121 in the receptacle 104 defined between the double jaw teeth 102 of the first clasp member 101 of the plier device 100a.

The component holder 126 positions and accommodates 706 the component 121 in the receptacle 104 defined between the double jaw teeth 102 of the first clasp member 101 of the plier device 100a based on one or more of the force commands received from the component configuration computer system 129. The position and direction contained in the force commands instructs the component holder 126 to rotate the component 121 to the appropriate coordinates. The clamping element 109 of the heat transfer clamp member 108 engages with the single jaw tooth 106 of the second clasp member 105 of the plier device 100a to detachably connect 707 the heat transfer clamp member 108 on the second clasp member 105. The heating coil 111 housed on the elongate member 110 of the heat transfer clamp member 108 generates 708 heat and transfers the generated heat to the single jaw tooth 106 of the second clasp member 105 of the plier device 100a via the clamping element 109 of the heat transfer clamp member 108 to heat the component 121. The single jaw tooth 106 of the second clasp member 105 of the plier device 100a contacts and electro-thermally heats 709 the component 121 positioned and accommodated within the receptacle 104 of the double jaw teeth 102 of the first clasp member 101 of the plier device 100a. In an embodiment, the single jaw tooth 106 contacts 709 and electro-thermally heats the component 121 positioned and accommodated within the receptacle 104 of the double jaw teeth 102 of the first clasp member 101 to about the threshold heating temperature of the material of the component 121.

The bending force transducer 128 controls 710 the magnitude and direction of the bending forces applied by the first clasp member 101 and the second clasp member 105 of the plier device 100a to precision bend and reshape the component 121 at one or more of the bending points 122a and 122b on the component 121 based on one or more of the force commands received from the component configuration computer system 129 to produce a desired curvature on the component 121. The precision of each bending force is produced by the series of force commands issued by the component configuration computer system 129 based on a three-dimensional curvature of the component 121. The temperature controller 112 controls 711 the generation of heat by the heating coil 111 and the transfer of the heat generated by the heating coil 111 to the single jaw tooth 106 of the second clasp member 105 of the plier device 100a to heat the component 121 to about the threshold heating temperature of the material of the component 121 and facilitate the temperature controlled, precision bending and reshaping of the component 121 in contact with the single jaw tooth 106 of the second clasp member 105.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A method for a temperature controlled, precision bending and reshaping of a component, said method comprising:
providing a precision configuration system comprising:
a container of a predefined shape, said container comprising an inner space and an opening positioned on a side of said container;
a component holder positioned in said inner space of said container, said component holder comprising a sleeve axially positioned and removably attached to said opening of said container;
a plier device positioned within said inner space of said container, said plier device comprising:
a first clasp member comprising double jaw teeth connected to a first jaw arm, said double jaw teeth defining a receptacle; and
a second clasp member hingedly connected to said first clasp member, said second clasp member comprising a single jaw tooth connected to a second jaw arm;
a heat transfer clamp member positioned within said inner space of said container, said heat transfer clamp member comprising:
a clamping element configured to engageably connect with said single jaw tooth of said second clasp member of said plier device;
an elongate member extending from a lower end of said clamping element; and
a heating coil housed on said elongate member;
a bending force transducer positioned within said inner space of said container and operably connected to said first clasp member and said second clasp member of said plier device;
a temperature controller positioned within said inner space of said container and electrically connected to said heating coil of said heat transfer clamp member; and a component configuration computer system comprising at least one processor in operable communication with said component holder and said bending force transducer;
calculating bending force data comprising a position, a direction, and a magnitude of each of a plurality of bending forces to be applied by said first clasp member and said second clasp member of said plier device to one or more of a plurality of bending points on said component, by said component configuration computer system using a three-dimensional first derivative and a three-dimensional second derivative of a curvature of said component;
converting said calculated bending force data at said bending points of said component into force commands by said component configuration computer system;
transmitting one or more of said force commands to said component holder and said bending force transducer by said component configuration computer system;
receiving said component via said sleeve of said component holder to advance and position said component in said receptacle defined between said double jaw teeth of said first clasp member of said plier device;
positioning and accommodating said component in said receptacle defined between said double jaw teeth of said first clasp member of said plier device by said component holder based on said one or more of said force commands received from said component configuration computer system;
detachably connecting said heat transfer clamp member on said second clasp member of said plier device by engaging said clamping element of said heat transfer clamp member with said single jaw tooth of said second clasp member;
generating heat via said heating coil housed on said elongate member of said heat transfer clamp member and transferring said generated heat to said single jaw tooth of said second clasp member of said plier device via said clamping element of said heat transfer clamp member;
contacting and electro-thermally heating said component positioned and accommodated within said receptacle of said double jaw teeth of said first clasp member of said plier device by said single jaw tooth of said second clasp member of said plier device;
controlling said magnitude and said direction of said bending forces applied by said first clasp member and said second clasp member of said plier device by said bending force transducer to precision bend and reshape said component at said one or more of said bending points on said component based on said one or more of said force commands received from said component configuration computer system; and
controlling said generation of said heat by said heating coil and said transfer of said generated heat to said single jaw tooth of said second clasp member of said plier device, by said temperature controller to heat said component to a threshold heating temperature of a material of said component and facilitate said temperature controlled, precision bending and said reshaping of said component in said contact with said single jaw tooth of said second clasp member.

2. The method of claim 1, further comprising moving said component holder in relation to said direction of said bending forces based on said one or more of said force commands received from said component configuration computer system to configurably position said component in said receptacle of said plier device.

3. The method of claim 1, further comprising directing a laser beam to one of said bending points on said component and transmitting a predefined amount of heat to said one of said bending points on said component by a laser precision heater positioned within said inner space of said container and in communication with said component configuration computer system, based on one or more of said force commands received from said component configuration computer system.

4. The method of claim 3, further comprising receiving initiation and termination commands by said laser precision heater from said component configuration computer system to initiate and terminate said transmission of said predefined amount of said heat to said one of said bending points on said component based on said one or more of said force commands received from said component configuration computer system.

5. The method of claim 3, further comprising monitoring temperature at said bending points on said component by an infrared temperature detector positioned within said inner space of said container, and communicating with said component configuration computer system to adjust said transmission of said predefined amount of said heat from said laser beam directed by said laser precision heater to said bending points on said component.

* * * * *